United States Patent [19]
Musser

[11] Patent Number: 6,150,539
[45] Date of Patent: Nov. 21, 2000

[54] TRIPTOLIDE PRODRUGS HAVING HIGH AQUEOUS SOLUBILITY

[75] Inventor: John H. Musser, San Carlos, Calif.

[73] Assignee: Pharmagenesis, Inc., Palo Alto, Calif.

[21] Appl. No.: 09/389,769

[22] Filed: Sep. 2, 1999

Related U.S. Application Data

[60] Provisional application No. 60/098,809, Sep. 2, 1998.

[51] Int. Cl.$^7$ .................................................. C07D 307/77
[52] U.S. Cl. ........................ 549/456; 549/218; 549/297; 549/543; 544/148; 536/1.11; 536/4.1
[58] Field of Search ..................................... 549/297, 432, 549/543, 456; 536/1.11, 4.1; 544/148

[56] References Cited

U.S. PATENT DOCUMENTS 5,972,998  10/1999  Jung et al. .............................. 514/468

FOREIGN PATENT DOCUMENTS 3178977A  9/1989  Japan .

OTHER PUBLICATIONS

Yu, D Q et al "Structure Modification of Triptolide" CA 118: 182770 (1993).

Primary Examiner—Amelia A. Owens
Attorney, Agent, or Firm—LeeAnn Gorthey

[57] ABSTRACT

Compounds useful in immunosuppressive and anti-inflammatory treatment are described. The compounds are hydrolyzable triptolide analogs with improved water solubility and generally lower toxicity than the parent compound.

8 Claims, 6 Drawing Sheets

TRIPTOLIDE PRODRUGS HAVING HIGH AQUEOUS SOLUBILITY

The present application claims the benefit of U.S. Provisional Application Ser. No. 60/098,809, filed Sep. 2, 1998, which is hereby incorporated by reference.

FIELD OF THE INVENTION

The present invention relates to compounds useful as immunosuppressive and anti-inflammatory agents. The compounds have good aqueous solubility and convert to biologically active compounds in vivo.

REFERENCES

Ferrier, R. J. in *CARBOHYDRATE CHEMISTRY*, Kennedy, J. F., Ed., Clarendon Press, Oxford (1990).
Garver, L. C. et al., *J. Am. Chem. Soc.* 104:867 (1982).
Gleichmann, E. et al., *Immunol. Today* 5:324 (1984).
Hormi, O. E. O. and Nasman, J. H., *Syn. Commun.* 16:69 (1986).
Kocienski, P. J., *PROTECTING GROUPS*, Georg Thieme Verlag, Stuttgart (1994).
Korngold, R. and Sprent, J., *J. Exp. Med.* 148:1687 (1978).
Kupchan, S. M. et al., *J. Am. Chem. Soc.* 94:7194 (1972).
Kupchan, S. M. et al., U.S. Pat. No. 3,005,108 (1977).
Lipsky, P. E. et al., U.S. Pat. No. 5,294,443 (1994).
Ma, P-C. et al., *J. Chin. Pharm. Sci.* 1:12 (1992).
Mori, S. et al., *Tetrahedron* 47(27):5051–5070 (1991).
Morris, R. E., *Transplant Proc.* 23(6):2722–2724 (1991).
Morris, R. E. et al., *Transplant Proc.* 23(1):238–240 (1991).
Murase, N. et al., *Transplantation* 55:701 (1993).
Ono and Lindsey, *J. Thor. Cardiovasc. Surg.* 57(2):225–29 (1969).
Pu, L. et al., *Zhongguo Yaoli Xuebao* 11:76 (1990).
Wang, J. and Morris, R. E., *Transplantation Proc.* 23:699 (1991).
Yu et al., *Acta Pharmaceutica Sinica* 27(11):830–836 (1992).
Zheng, J. et al., *Zhongguo Yixue Kexueyuan Xuebao* 13:391 (1991).
Zheng, J. et al., *Zhongguo Yixue Kexueyuan Xuebao* 16:24 (1994).

BACKGROUND OF THE INVENTION

Immunosuppressive agents are widely used in the treatment of autoimmune disease and in treating or preventing transplantation rejection, including the treatment of graft-versus-host disease (GVHD), a condition in which transplanted marrow cells attack the recipient's cells. Common immunosuppressive agents include azathioprine, corticosteroids, cyclophosphamide, methotrexate, 6-mercaptopurine, vincristine, and cyclosporin A. In general, none of these drugs are completely effective, and most are limited by severe toxicity. For example, cyclosporin A, a widely used agent, is significantly toxic to the kidney. In addition, doses needed for effective treatment may increase the patient's susceptibility to infection by a variety of opportunistic invaders.

A number of compounds isolated from the Chinese medicinal plant *Tripterygium wilfordii* (TW) have been identified as having immunosuppressive activity. Representative compounds include triptolide, 16-hydroxytriptolide, triptophenolide, tripdiolide, and tripchlorolide, as described, for example, in Lipsky et al. (1994) and Zheng et al. (1991; 1994).

The administration and therapeutic effectiveness of these compounds have been limited, however, by their low water solubility. This problem has been addressed by formulating the compounds in mixtures of ethanol and polyethoxylated castor oil (e.g., "CREMOPHOR EL™"), allowing subsequent dilution in saline for intravenous administration. However, such formulations have suffered from high toxicity, due to the high concentration of solubilizing agent required to dissolve these compounds. For example, the ratio of solubilizing agent (ethanol plus "CREMOPHOR EL™") to triptolide in such formulations is typically on the order of 1000:1 or greater, due to the poor solubility of triptolide (Morris, 1991; Morris et al., 1991). Standardization of dosage amounts is also more problematic with a suspension than with a solution.

It is therefore desirable to provide immunosuppressive compounds having comparatively low toxicity and improved water solubility. Ideally, such compounds would show immunosuppressive activity in their water soluble form, or would be convertible to an immunosuppressive form in vivo.

SUMMARY OF THE INVENTION

In one aspect, the invention provides compounds which are useful as prodrugs for immunosuppressive and anti-inflammatory therapy. The compounds are derivatives of triptolide having hydrophilic substituents, represented by structures I–III, as shown and described below. The compounds possess greater water solubility than the non-derivatized parent compound, triptolide, and are effective to hydrolytically convert to the parent compound in vivo.

These and other objects and features of the invention will become more fully apparent when the following detailed description of the invention is read in conjunction with the accompanying drawings.

DETAILED DESCRIPTION OF THE INVENTION

I. Definitions

Figure 1:
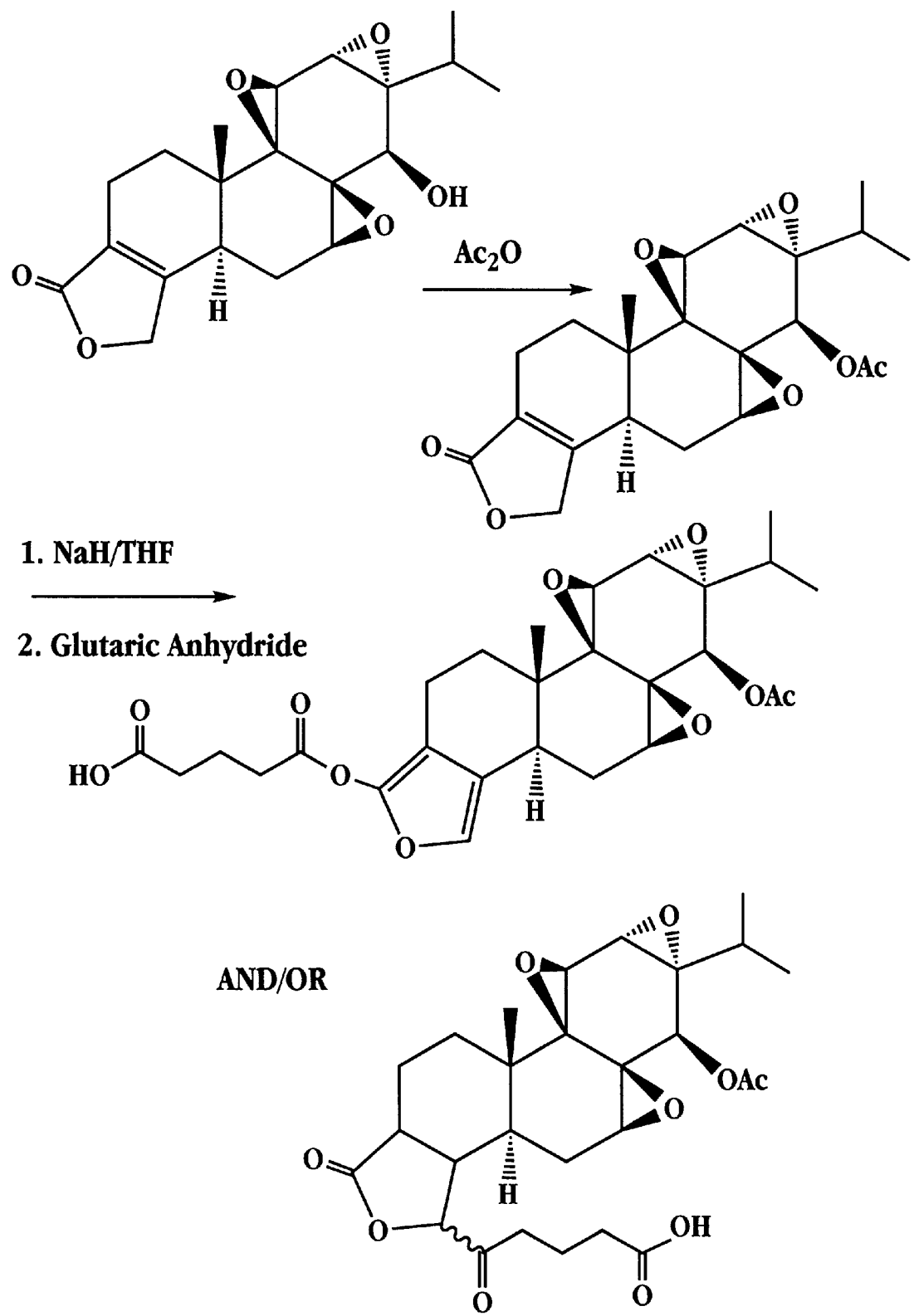
FIG. 1 shows the preparation of triptolide derivatized at the lactone ring, in accordance with structure I.

The terms below have the following meanings unless indicated otherwise.

"Alkyl" refers to a fully saturated acyclic monovalent radical containing carbon and hydrogen, which may be branched or a straight chain. Examples are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples are cyclopropyl, methyl cyclopropyl, cyclobutyl, cyclopentyl, and cyclohexyl. "Lower alkyl" refers to an alkyl radical of one to six carbon atoms, as exemplified by methyl, ethyl, n-butyl, i-butyl, t-butyl, isoamyl, n-pentyl, and isopentyl.

"Alkenyl" refers to a monovalent or divalent unsaturated, preferably mono-unsaturated, radical containing carbon and hydrogen, and which may be cyclic, branched or a straight chain. "Lower alkenyl" refers to such a radical having one to four carbon atoms.

A "triptolide derivative" or "triptolide analog," as described herein, refers to a compound based on triptolide, 16-hydroxytriptolide or tripdiolide (2-hydroxytriptolide) which is derivatized at the 12,13-epoxy group or at the lactone ring of the parent compound.

For the purposes of the current disclosure, the following numbering scheme is used for triptolide and triptolide analogs:

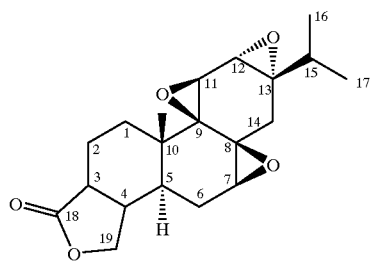

II. Triptolide Analogs

This section describes the preparation of compounds as represented by structures I–III and described further below. The present compounds, which are derivatives of triptolide having hydrophilic substituents, possess greater water solubility than the non-derivatized starting compound, and are effective to hydrolyze and convert in vivo to the parent compound. The compounds are useful as prodrugs for immunosuppressive and anti-inflammatory applications. Although each of structures I–III shows a compound modified at one location on the triptolide nucleus, compounds having more than one such modification are also contemplated.

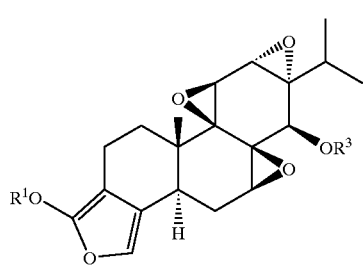

I

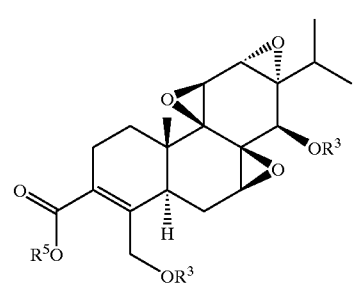

II

-continued

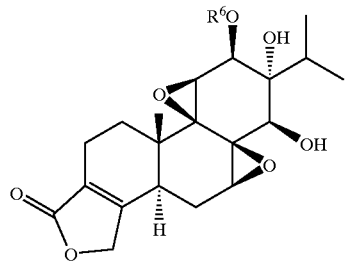

III

The compounds of the invention may be prepared from triptolide, as obtained from the root xylem of the Chinese medicinal plant *Tripterygium wilfordii* (TW) or from other known sources. The TW plant is found in the Fujiang Province and other southern provinces of China; TW plant material can generally be obtained in China or through commercial sources in the United States. Methods for preparing triptolide and some of its derivatives (e.g. tripdiolide and 16-hydroxytriptolide) are known in the art and are described, for example, in Kupchan et al. (1972, 1977); Lipsky et al. (1994); Pu et al. (1990); and Ma et al. (1992).

A. Compounds of Structure I

In the compounds of structure I, $OR^1$ is a hydrolyzable, hydrophilic group, e.g. a carboxylic ester, an inorganic ester, or a mono-, di- or trisaccharide linked to the parent compound via an anomeric oxygen. The carboxylic or inorganic ester has a central atom selected from carbon, sulfur, phosphorus, and boron, and attached to the central atom, at least one oxygen atom, and at least one group of the form —O—Y—Z. In this group, Y represents a branched or unbranched $C_1$–$C_6$ alkyl or alkenyl chain, and Z represents hydrogen, or, preferably, a polar group selected from keto, aldehyde, carboxylate, carboxylic ester, hydroxy, alkoxy, polyether, thiol, alkylthio, amino, alkylamino, cyano, nitro, sulfate, nitrate, phosphate, or a 5- to 7-membered heterocyclic ring whose ring atoms are selected from the group consisting of carbon, nitrogen, heterocycles include, for example, pyridine, pyrrolidine, piperazine, and morpholine.

Examples of such inorganic esters include sulfites (—O—S(=O)—OR), sulfinates (—O—S(=O)—R), sulfates (—O—S(=O)$_2$—OR), sulfonates (—O—S(=O)$_2$—R), phosphates (—O—P(=O)(OR)$_2$), phosphonates (—O—P(=O)R(OR)), and borates (—O—B(OR)$_2$).

Where Z is an anionic species such as a carboxylate, the positively charged counterion is preferably an inorganic metal, such as $Na^+$, $K_+$, or $Mg^{+2}$, or a protonated organic amine, e.g. tromethamine (tris(hydroxymethyl) aminomethane). Where Z is a basic amine, the compound may take the form of a protonated salt, with a negatively charged counterion such as chloride, bromide, iodide, acetate, oxalate, maleate, fumarate, mesylate or tosylate.

Preferably, $R^1$ is selected from:

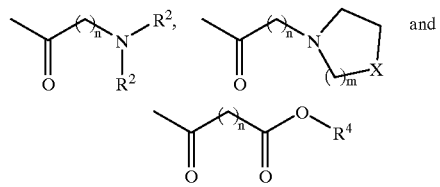

where $R^2$ is lower alkyl, $R^3$ is H or —(C=O)R, where R is lower alkyl, $R^4$ is H or lower alkyl, n=0–4, m=1–2, and $X=CH_2$, O, or $NR^2$. The substituent $OR^3$ is OH or O—(C=O)R, where R is lower alkyl.

The hydrophilic nature of the substituents increases the aqueous solubility of the compounds, and hydrolysis of $OR^1$ (e.g. in vivo) regenerates the unsaturated lactone (butenolide) of triptolide.

The compounds of structure I may be prepared by reaction of the unsaturated lactone (butenolide) with base, to generate the enolate, followed by alkylation with an electrophilic reagent such as $R^1$—X, where X is a displacable leaving group, or an activated acyl reagent, such as an acid chloride, anhydride, or carbonyl imidazole (see Hormi et al. and Garver et al.). See, for example, FIG. 1, where the butenolide enolate, prepared by reaction with sodium hydride in dry THF, is acylated with glutaric anhydride, to give the carboxylic acid-terminated ester derivative. Note that acylation may also occur at carbon to give a keto side product. In such cases, the products may be separated by conventional methods, e.g. column chromatography on silica gel.

Figure 2A:
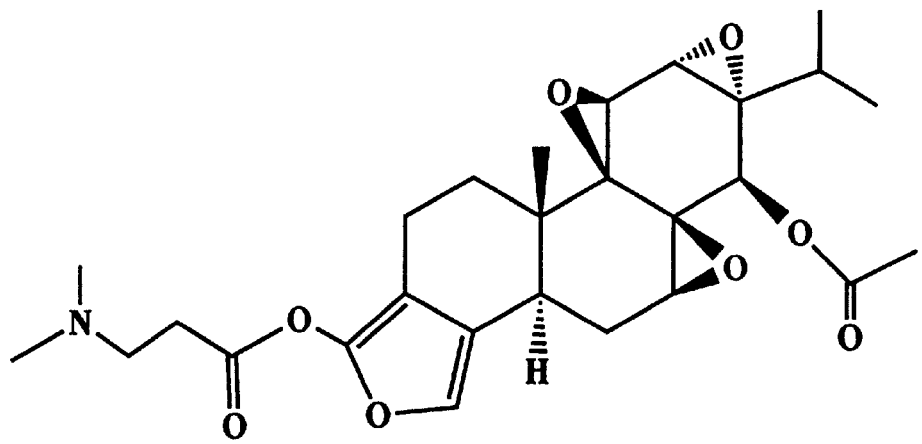
FIGS. 2A–2C show examples of specific embodiments of structure I.
Figure 2B:
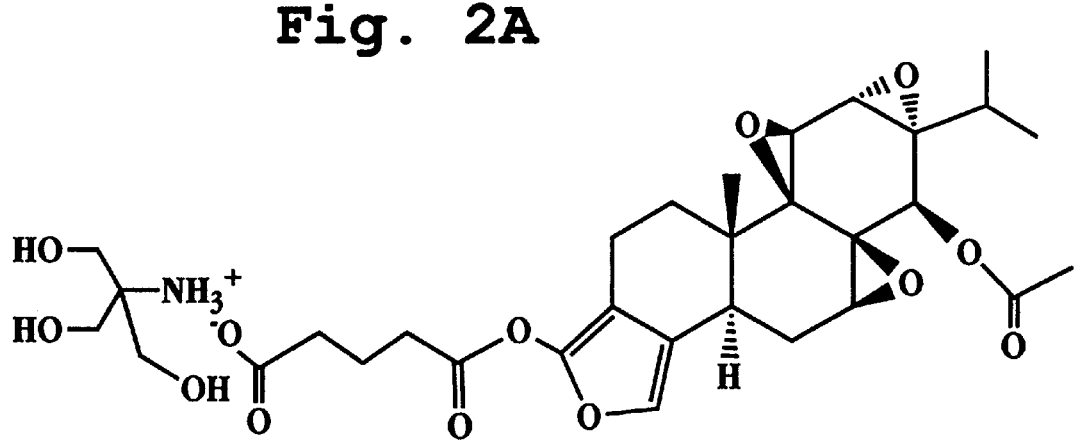
Figure 2C:
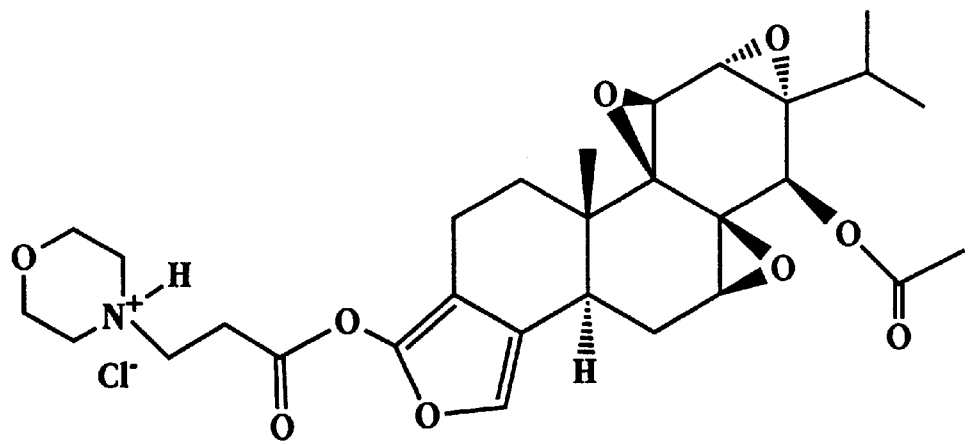

Reacting the terminal acid with tromethamine gives the salt shown in FIG. 2B. Other representative analogs of structure I are shown in FIGS. 2A and 2C.

Inorganic ester derivatives are prepared by similar base-catalyzed reaction of the butenolide with the appropriate activated inorganic acid derivative, such as a halide or an anhydride (e.g. $SO_3$). For preparation of glycosides, $R^1X$ is a glycosyl halide or other activated glycosyl derivative. One such type of derivative is an acetimidate activated glycoside, which may be prepared by reaction of a suitably protected glycosyl halide with a secondary amide in the presence of $Ag_2O$ and base (see e.g. Ferrier, in Kennedy, p. 352). In preparing this class of compounds, as well as those in accordance with structures II and III, below, it is generally desirable to protect the hydroxyl group at the 14 position. Therefore, $OR^3$ in these structures is hydroxyl or, preferably, —O(C=O)R, where R is lower alkyl. For ease of preparation, a simple ester such as acetyl is typically employed.

B. Compounds of Structure II

In another embodiment, the triptolide analogs are of the structure II, as shown above. The group $OR^3$ is as defined above, and is preferably lower acyl, e.g. acetyl. The group $OR^5$ is preferably of the form —O—Y—Z or —O—(C=O)—Y—Z, where Y is a branched or unbranched $C_1$–$C_6$ alkyl or alkenyl chain, and Z is hydrogen or a polar group selected from keto, aldehyde, carboxylate, carboxylic ester, amino, alkylamino, hydroxy, alkoxy, polyether, thiol, alkylthio, cyano, nitro, inorganic ester, or a 5- to 7-member heterocyclic ring whose ring atoms are selected from the group consisting of carbon, nitrogen, oxygen and sulfur, where the ring atoms include 3 to 6 carbon atoms. $R^5$ may also be a mono-, di- or trisaccharide linked to C14 at an anomeric center.

Again, where Z is an anionic species such as a carboxylate, the positively charged counterion is preferably an inorganic metal, such as $Na^+$, $K^+$, or $Mg^{+2}$, or a protonated organic amine, e.g. tromethamine. Where Z is a basic amine, the compound may take the form of a protonated salt, with a negatively charged counterion such as chloride, bromide, iodide, acetate, oxalate, maleate, fumarate, mesylate or tosylate.

Preferably, $R^5$ is of the form:

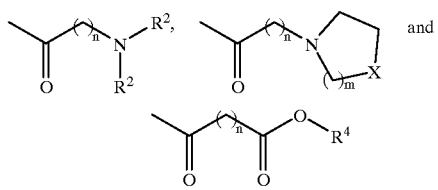

where $R^2$ is lower alkyl, $R^3$ is —(C=O)R, where R is lower alkyl, $R^4$ is H or lower alkyl, p=0–6, m=1–2, n=1–4, and $X=CH_2$, O, or $NR^2$.

Figure 3:
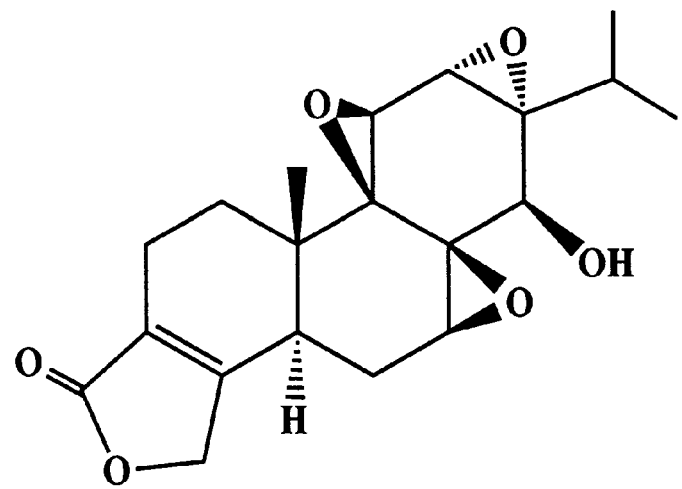
FIG. 3 shows the preparation of a lactone ring-opened derivative of triptolide, in accordance with structure II.
Figure 3:
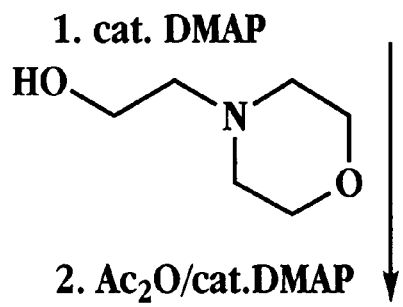
Figure 3:
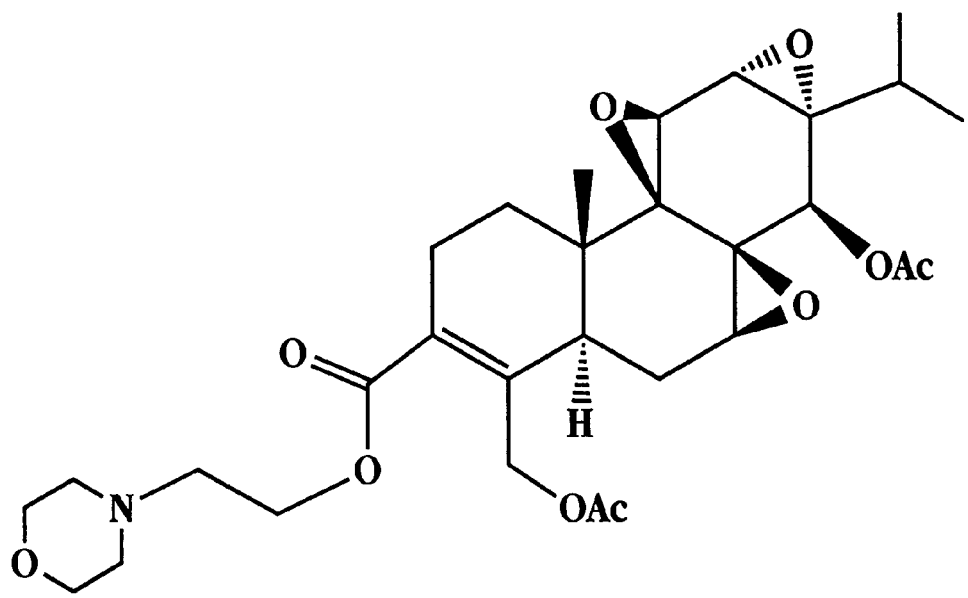

These compounds are prepared by transesterification of the lactone ring of triptolide with a hydroxyl-containing compound. A hydrophilic alcohol (e.g., a saccharide, or a substituted heterocycle as shown in FIG. 3) is preferably used for the transesterification, to increase the water solubility of the resulting compound. The hydroxyl generated on ring opening of the lactone is reacted with, for example, an acid chloride, as shown, to give a hydrolyzable group, such as an ester, from which the alcohol may be regenerated hydrolytically in vivo.

Figure 4A:
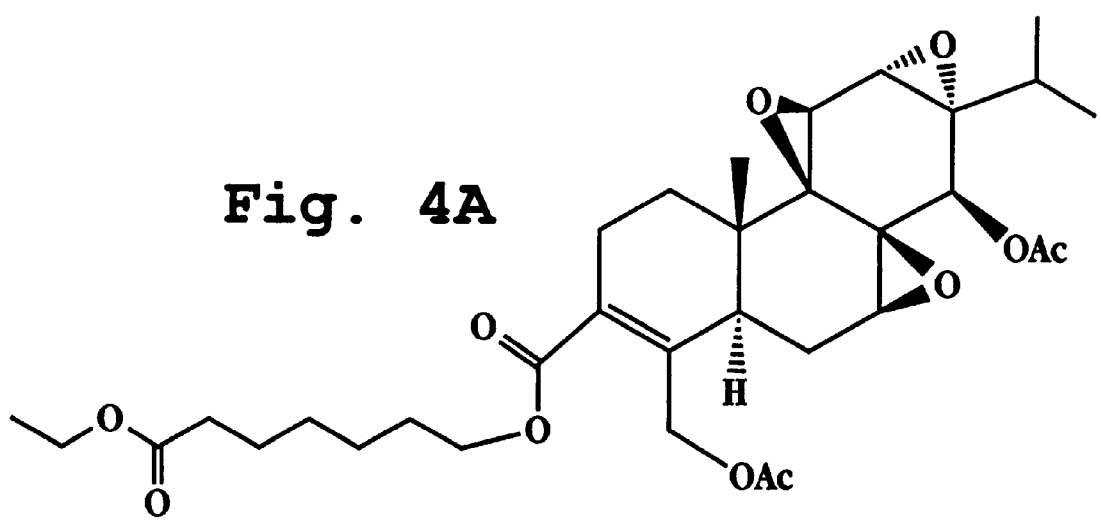
FIGS. 4A–4C show examples of specific embodiments of structure II.
Figure 4B:
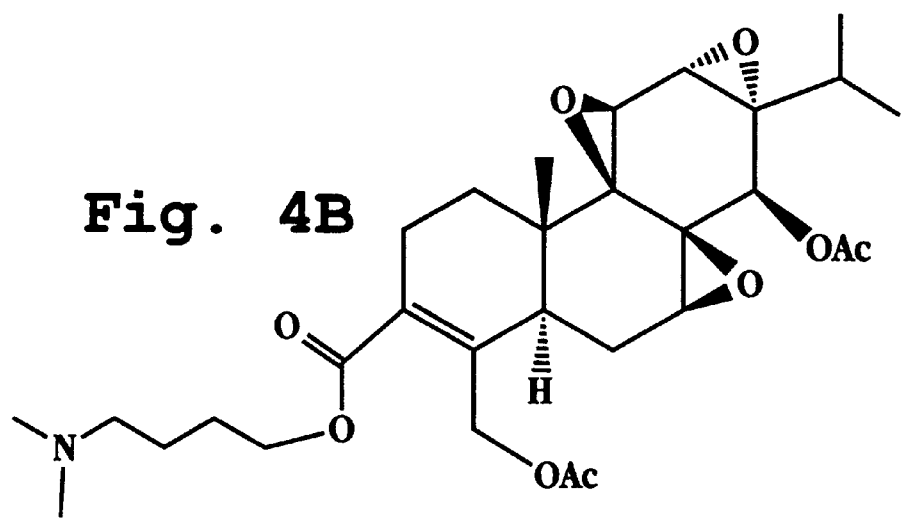
Figure 4C:
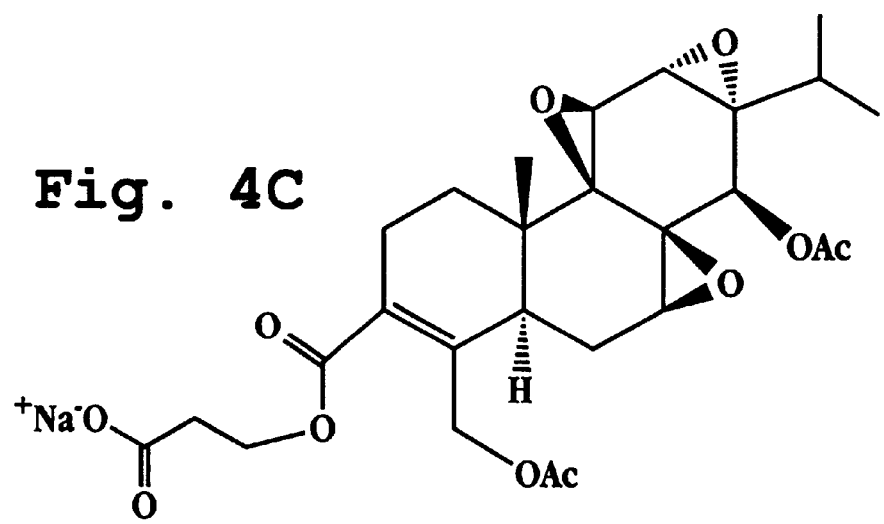

A typical synthesis is shown in FIG. 3, in which triptolide is reacted with 1-(2-hydroxyethyl)-morpholine in the presence of a catalytic amount of DMAP. The free hydroxyl group which is generated, as well as the free 14-hydroxyl, are then acylated to give the final compound. Further examples are shown in FIGS. 4A–4C. When such a compound is administered as a prodrug, the ester groups are hydrolytically cleaved in vivo, and the ester and alcohol at the 3 and 4 positions react to regenerate the lactone ring of triptolide.

C. Compounds of Structure III

In a further embodiment, the triptolide analogs have the structure III, as shown above, where $R^6$ is a leaving group selected from the group consisting of alkyl sulfonate, fluoroalkyl sulfonate, aryl sulfonate, fluorosulfonate, nitrate, alkyl phosphate, alkyl borate, trialkylammonium, and dialkylsulfonium. Preferred leaving groups are tosylate, mesylate, fluorosulfonate, trifluoromethylsulfonate, nitrate, and alkyl phosphates or boronates, represented by —OP(O)$(OR^4)_2$, and —OB$(OR^4)_2$, where $R^4$ is hydrogen or lower alkyl. The group $OR^3$ is —OH or —O—(C=O)—R, where R is lower alkyl.

Figure 5:
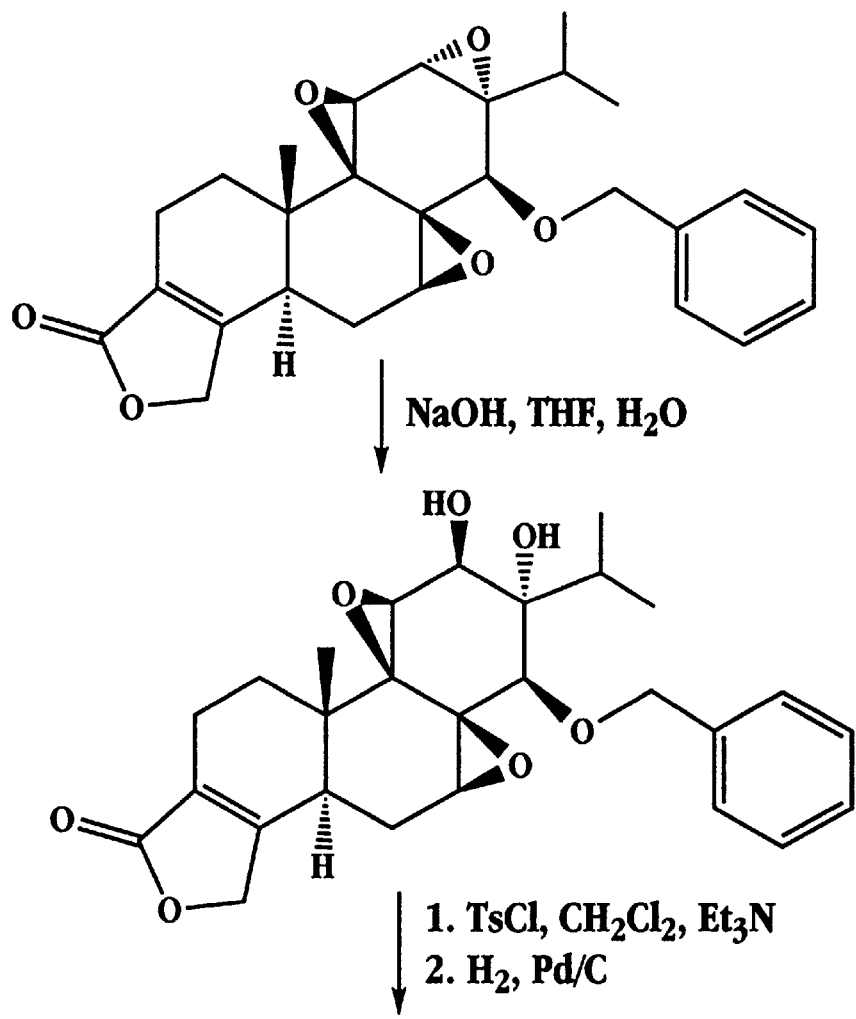
FIG. 5 shows the preparation of an epoxy ring-opened derivative of triptolide, in accordance with structure III.

These compounds are prepared by base-catalyzed ring opening of the 12,13 epoxy group of triptolide, as illustrated in FIG. 5. As noted in Yu et al., the 12,13 epoxide of triptolide is less sterically hindered and reacts more readily than the 7,8 and 9,11 epoxides. The epoxide is regenerated in vivo by displacement of the 12-leaving group, restoring the triptolide structure.

Figure 6A:
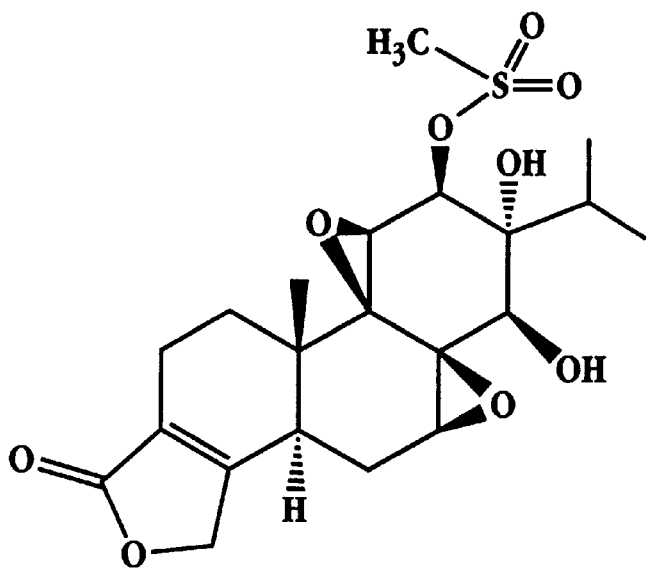
FIGS. 6A–6C show examples of specific embodiments of structure III.
Figure 6B:
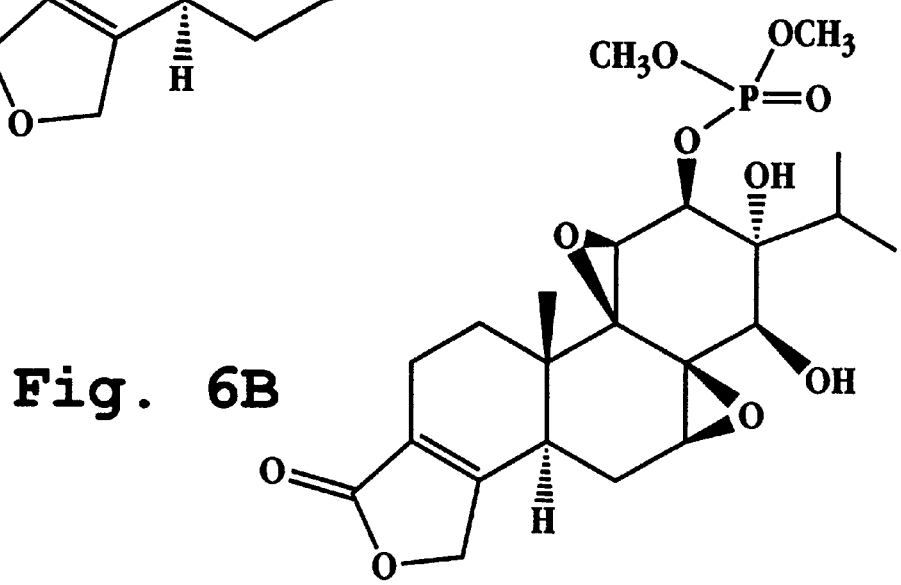
Figure 6C:
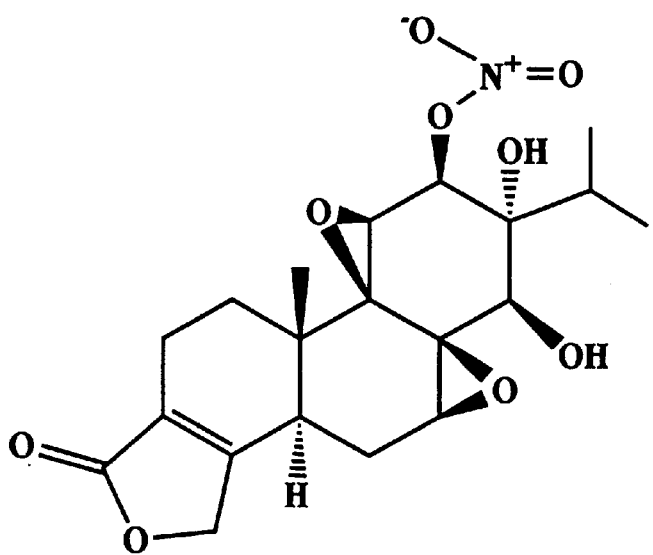

In the synthesis shown in FIG. 5, the hydroxyl at C14 is first protected as a benzyl ether, which is later removed by hydrogenation. The nucleophile, typically hydroxide ion, attacks at the less hindered 12-carbon of the epoxide. The resulting 12-hydroxyl group of the 1,2-diol is then converted to the leaving group $R^6$, in this case a tosylate. Other examples of compounds of structure III are shown in FIGS. 6A–6C.

If desired, the 13-hydroxyl (and 14-hydroxyl) may be converted to a hydrolyzable group, so that the compound will be more stable upon storage, but will still convert (albeit more slowly) to the epoxide in vivo. Because the 13-hydroxyl is tertiary and thus slow to react, use of an unhindered, reactive acylating agent, e.g., acetyl chloride, is preferred.

III. Therapeutic Compositions

Formulations containing the triptolide analogs of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide analog in a suitable intravenous solution, such as sterile physiological salt solution.

Liquid compositions can be prepared by dissolving or dispersing the triptolide analog (about 0.5% to about 20%) and optional pharmaceutical adjuvants in a carrier, such as, for example, aqueous saline, aqueous dextrose, glycerol, or ethanol, to form a solution or suspension. The high water solubility of the compounds of the invention make them particularly advantageous for administering in aqueous solution, e.g. by intraperitoneal injection. Although aqueous solutions are preferred, compositions in accordance with the invention may also be formulated as a suspension in a lipid (e.g., a triglyceride, a phospholipid, or a polyethoxylated castor oil such as "CREMOPHOR EL™"), in a liposomal suspension, or in an aqueous emulsion.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in a pharmaceutically effective amount for effecting immunosuppression in a subject.

IV. Therapeutic Uses

The compositions of the present invention are useful in applications for which triptolide has proven effective, particularly in immunosuppression therapy, as in treating an autoimmune disease, preventing transplantation rejection, or treating or preventing graft-versus-host disease (GVHD). Triptolide and the present analogs are also useful for treatment of other inflammatory conditions, such as traumatic inflammation, and in reducing male fertility.

Common autoimmune diseases which are appropriate for immmunotherapy include asthma, atherosclerosis, Type I diabetes, multiple sclerosis, psoriasis, systemic lupus erythematosis (SLE), rheumatoid arthritis, and various allergies. In treating an autoimmune condition, the patient is given the composition on a periodic basis, e.g., 1–2 times per week, at a dosage level sufficient to reduce symptoms and improve patient comfort.

The dose that is administered is preferably in the range of 1–25 mg/kg patient body weight per day, with lower amounts being preferred for parenteral administration, and higher amounts being preferred for oral administration. Optimum dosages can be determined by routine experimentation according to methods known in the art.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal $F_1$ mice with parental spleen cells; the mice develop a GVHD syndrome characterized by splenomegaly and immunosuppression (Korngold, 1978; Gleichmann, 1984). Single cell suspensions are prepared from individual spleens, and microwell cultures are established in the presence and absence of concanavalin A to assess the extent of mitogenic responsiveness.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogenic lymphocytes, or by taking a biopsy of the transplanted tissue.

In addition, the composition may be administered chronically to prevent graft rejection, or in treating acute episodes of late graft rejection. As above, the dose administered is preferably 1–25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

For treating rheumatoid arthritis, the composition may be administered by intravenous injection or by direct injection into the affected joint. The patient may be treated at repeated intervals of at least 24 hours, over a several week period following treated at repeated intervals of at least 24 hours, over a several week period following the onset of symptoms of the disease in the patient.

The compounds are also useful as potentiators when administered concurrently with another immunosuppressive drug for immunosuppressive treatments as discussed above. A conventional immunosuppressant drug, such as cyclosporin A, FK506, azathioprine, rapamycin, mycophenolic acid, or a glucocorticoid, may thus be administered in an amount substantially less (e.g. 20% to 50% of the standard dose) than when the compound is administered alone. Alternatively, the triptolide analog and immunosuppresive drug are administered in amounts such that the resultant immunosuppression is greater than what would be expected or obtained from the sum of the effects obtained with the drug and triptolide analog used alone. Typically, the immunosuppressive drug and potentiator are both administered at regular intervals over a time period of at least 2 weeks.

EXAMPLES

The following examples are intended to illustrate but not in any way limit the invention. While the invention has been described with reference to specific methods and embodiments, it will be appreciated that various modifications may be made without departing from the invention.

Example 1

Synthesis of 18-Glutaryl Furanoid Triptolide Analog (FIG. 1) and Tromethamine Salt (FIG. 2B)

Triptolide (1 eq.) in dry THF is added dropwise, under an inert atmosphere, to a stirred suspension of a slight excess of NaH in dry THF at −78° C. After approx. 0.5 hr, glutaric anhydride (1 eq. or slight excess) is added dropwise, and the stirred mixture is allowed to come to room temperature over approx. 1 hr. The mixture is concentrated, taken up in ether, washed with water and brine, dried over anhydrous $MgSO_4$ and concentrated. The residue is purified by chromatography on silica gel.

To a stirred solution of 1 eq. of the glutaryl ester in THF is added a slight excess of a methanolic solution of tromethamine. The solution is concentrated, and the salt is recovered and dried under vacuum.

Example 2

Synthesis of Lactone Ring Opened Triptolide Analog (FIG. 3)

A solution of triptolide, excess (2-hydroxyethyl) morpholine and a catalytic amount of DMAP (dimethylaminopyridine) is stirred with mild heating in a polar aprotic solvent such as THF. The reaction is monitored by TLC. Upon completion, the reaction mixture is cooled, and acetic anhydride is added to acetylate the 14- and 19-hydroxyl groups. The solvent is removed under reduced pressure, and the residue is taken up in ether, washed several times with water and sodium bicarbonate solution, dried over anhydrous $MgSO_4$ and concentrated. If necessary, the product is purified by silica gel chromatography.

Example 3

Synthesis of 12-tosloxy-13-hydroxy triptolide (FIG. 5)

The 14-hydroxyl group is first protected by conversion to a benzyl ether. To avoid reaction of the acidic hydrogens of the conjugated lactone with basic reagents, such as metal hydrides, the compound (1 eq) is reacted with BzBr (2.5 eq) in the presence of $Ag_2O$ (2 eq) in DMF under an inert atmosphere at 0° C. (see, for example, Mori et al.). The mixture is allowed to come to room temperature with stirring and stirred for about 24 h. The mixture is diluted with ether, washed with water and brine, dried over anhydrous $MgSO_4$ and concentrated. The residue is purified, if desired, by chromatography on silica gel.

The resulting 14-O-benzyl triptolide is then heated with NaOH in aqueous THF to convert the 12,13 epoxide to the diol. The solution is concentrated and the residue taken up in ether and worked up as above.

The diol (1 eq) is dissolved in $CH_2Cl_2$, and a solution of TsCl (1.5 eq) and triethylamine (1.5 eq) in the same solvent is added. After the reaction is complete by TLC, the mixture is washed with water and brine, dried over anhydrous $MgSO_4$, and concentrated. The residue is purified by silica gel chromatography.

The resulting benzyl ether-protected tosylate is dissolved in dry THF, 5% Pd/C (approx. 25 mg/meq of substrate) is added, and the mixture is purged with $H_2$ (atmospheric pressure) and stirred at room temperature until deprotection is complete, approx. 2–3 hrs. The solution is then filtered and concentrated to obtain the product.

It is claimed:

1. A compound having the structure I:

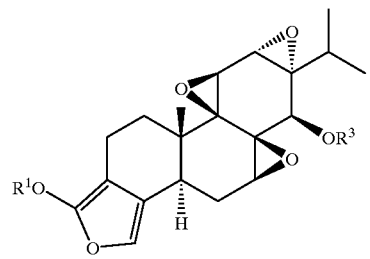

where $OR^1$ is selected from (i) a carboxylic ester, carbonate, or inorganic ester, having a central atom selected from carbon, sulfur, phosphorus, nitrogen, and boron, and having linked to said central atom at least one group of the form —Y—Z or —O—Y—Z, where Y is a branched or unbranched $C_1$–$C_6$ alkyl or alkenyl chain, and Z is hydrogen or a polar group selected from keto, aldehyde, carboxylate, carboxylic ester, hydroxy, alkoxy, polyether, thiol, alkylthio, amino, cyano, nitro, sulfate, nitrate, phosphate, or a 5- to 7-membered heterocycle having ring atoms selected from carbon, nitrogen, oxygen, and sulfur, and three to six carbon ring atoms, and (ii) a mono-, di- or trisaccharide linked to C14 at an anomeric center;

and $OR^3$ is OH or O—(C=O)R, where R is lower alkyl.

2. A compound in accordance with claim 1, wherein $R^1$ is selected from group (i).

3. A compound in accordance with claim 2, where $R^1$ is selected from

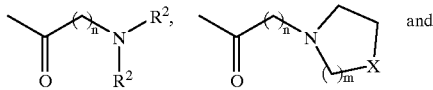

-continued

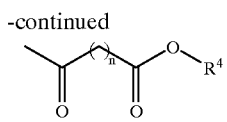

where
R² is lower alkyl,
R³ is H or —(C=O)R, where R is lower alkyl,
R⁴ is H or lower alkyl,
n=1–4,
m=1–2, and
X=CH₂, O, or NR².

4. A compound having the structure II:

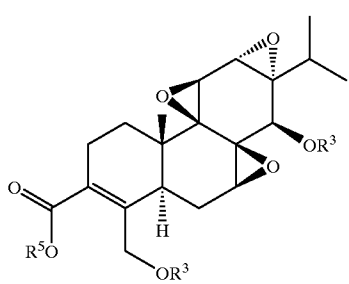

where OR⁵ is selected from
(i) —O—Y—Z or —O—(C=O)—Y—Z, where Y is a branched or unbranched C₁–C₆ alkyl or alkenyl chain, and Z is hydrogen or a polar group selected from keto, aldehyde, carboxylate, carboxylic ester, amino, alkylamino, hydroxy, alkoxy, polyether, thiol, alkylthio, cyano, nitro, inorganic ester, or a 5- to 7-member heterocyclic ring whose ring atoms are selected from the group consisting of carbon, nitrogen, oxygen and sulfur, where the ring atoms include 3 to 6 carbon atoms, and
(ii) a mono-, di- or trisaccharide linked to C14 at an anomeric center;
and OR³ is —O—(C=O)R, where R is lower alkyl.

5. A compound in accordance with claim 4, where R⁵ is selected from group (i).

6. A compound in accordance with claim 5, where R⁵ is selected from:

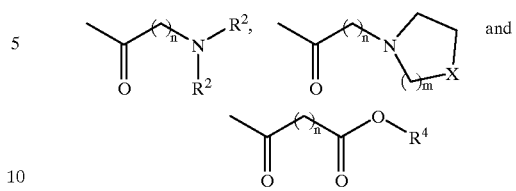

where
R² is lower alkyl,
R³ is —(C=O)R, where R is lower alkyl,
R⁴ is H or lower alkyl,
n=1–4,
m=1–2, and
X=CH₂, O, or NR².

7. A compound having the structure III:

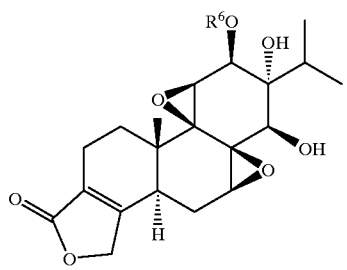

where
R⁶ is a leaving group selected from the group consisting of alkyl sulfonate, fluoroalkyl sulfonate, aryl sulfonate, fluorosulfonate, nitrate, alkyl phosphate, alkyl borate, trialkylammonium, and dialkylsulfonium.

8. A compound in accordance with claim 7, wherein OR⁶ is selected from nitrate, tosylate, mesylate, fluorosulfonate, trifluoromethylsulfonate, —OP(O)(OR⁴)₂, and —OB(OR⁴)₂, where R⁴ is hydrogen or lower alkyl.

* * * * *